US006772764B2

(12) United States Patent
Chapman

(10) Patent No.: US 6,772,764 B2
(45) Date of Patent: Aug. 10, 2004

(54) APPARATUS AND METHOD FOR TRANSPORTING AND SECURING A RESTRAINED PERSON

(75) Inventor: Bruce Chapman, Gardiner, NY (US)

(73) Assignee: Handle With Care, Inc., Gardiner, NY (US)

( * ) Notice: Subject to any disclaimer, the term of this patent is extended or adjusted under 35 U.S.C. 154(b) by 69 days.

(21) Appl. No.: 10/265,944

(22) Filed: Oct. 7, 2002

(65) Prior Publication Data

US 2003/0066134 A1 Apr. 10, 2003

Related U.S. Application Data

(60) Provisional application No. 60/327,618, filed on Oct. 6, 2001.

(51) Int. Cl.[7] .................................................. A61F 5/37

(52) U.S. Cl. .................... 128/870; 128/869; 128/87 R; 128/133; 128/134; 128/135; 128/846; 269/322; 269/328; 5/81 R; 5/624; 5/625; 5/626; 5/627; 5/628

(58) Field of Search .............................. 128/87 R, 846, 128/869, 870, 134, 133, 135; 269/322, 328; 5/81 R, 624, 625, 626, 627, 628

(56) References Cited

U.S. PATENT DOCUMENTS 3,641,997 A * 2/1972 Posey, Jr. .................. 128/873
3,829,914 A * 8/1974 Treat ......................... 5/81.1 T
3,875,599 A * 4/1975 Mracek et al. ................ 5/706
3,878,844 A * 4/1975 Tobias ........................ 128/876
4,132,229 A * 1/1979 Morrison .................... 128/876
D251,388 S * 3/1979 Burns et al. ............... D24/190
4,181,358 A * 1/1980 Pennington ................. 297/467
4,330,152 A * 5/1982 Legan et al. ................ 297/465
4,360,014 A * 11/1982 Manahan .................... 128/874
D275,230 S * 8/1984 Hubbard et al. ........... D24/190
4,519,106 A * 5/1985 Sandquist ...................... 5/652
4,608,973 A * 9/1986 Green et al. ................ 128/874
4,627,428 A * 12/1986 Brooks ....................... 128/873
4,653,131 A * 3/1987 Diehl ........................... 5/494
4,655,206 A * 4/1987 Moody .......................... 5/628
4,655,207 A * 4/1987 Ellis ........................... 128/871
4,742,821 A * 5/1988 Wootan ...................... 128/873
4,744,115 A * 5/1988 Marchione ................. 5/81.1 T
4,744,354 A * 5/1988 Triunfol ..................... 128/875
4,777,944 A * 10/1988 Green et al. ................ 128/874
4,840,189 A * 6/1989 Wachtel ...................... 128/869
4,853,996 A * 8/1989 Harrigan et al. ............... 5/494
4,858,625 A * 8/1989 Cramer ....................... 128/872
4,998,308 A * 3/1991 Farago .......................... 5/424
5,065,464 A * 11/1991 Blanchard et al. ......... 5/81.1 R
5,150,487 A * 9/1992 Hemphill ....................... 5/625

(List continued on next page.)

*Primary Examiner*—Henry Bennett
*Assistant Examiner*—Nihir Patel
(74) *Attorney, Agent, or Firm*—Edward Etkin, Esq.

(57) ABSTRACT

The transport and securing system of the present invention is utilized in conjunction with a wrist and ankle mechanical restraint system applied to a subject, which releasably secures the restrained subject to the transport and securing system, to easily and quickly transport the restrained subject and secure the subject to an ordinary bed, or any other stationary structure, without removing the subject's mechanical restraints. A instant release mechanism enables a single staff member to immediately disconnect the transport and securing system from the stationary structure so that the restrained subject may me quickly transported into another location without releasing the subject from the mechanical restraint system. The inventive transport and securing system includes optional releasable chest and stomach straps to supplement the mechanical restraint system. Alternately, the inventive transport and securing system may be configured to utilize an upper body protection and face shield system. When not in use, the inventive transport and securing system rolls up into a compact cylinder for convenient storage and transportation.

22 Claims, 7 Drawing Sheets

U.S. PATENT DOCUMENTS 5,190,055 A * 3/1993 O'Connor .................. 128/869
5,263,214 A * 11/1993 McLaughlin et al. .......... 5/628
5,274,864 A * 1/1994 Morgan ......................... 5/627
5,285,797 A * 2/1994 Zeller ............................ 5/628
5,317,770 A * 6/1994 Sakurai ......................... 5/625
5,524,306 A * 6/1996 George .......................... 5/424
D381,428 S * 7/1997 Torok et al. ............... D24/190
5,819,746 A * 10/1998 Walton ....................... 128/869
6,053,580 A * 4/2000 White, Sr. .................. 297/467
6,055,988 A * 5/2000 Perisho ....................... 128/869

* cited by examiner

APPARATUS AND METHOD FOR TRANSPORTING AND SECURING A RESTRAINED PERSON

REFERENCE TO PREVIOUSLY FILED APPLICATIONS

The present patent application claims priority from a previously filed commonly assigned U.S. Provisional Patent Application Serial No. 60/327,618, entitled “Apparatus and Method for Transporting and Securing a Restrained Person” filed on Oct. 6, 2001.

BACKGROUND OF THE INVENTION

The present invention is directed to a restrained person transport and securing system that, in conjunction with a mechanical restraint system, may be utilized to easily and quickly transport a restrained subject and secure the subject to an ordinary bed, or any other stationary structure, without removing the subject’s mechanical restraints.

There are many thousands of human service and law enforcement agencies and facilities that provide care and supervision to aggressive, suicidal, and emotionally disturbed persons (hereinafter commonly referred to as “EDPs”). The staff and officers working in these agencies regularly come into physical contact with the EDPs through the use of physical subduing or restraint holds when the EDP becomes aggressive. Although there are many types of well-known physical subduing holds, the safest and most advantageous physical subduing hold is a Primary Restraint Technique (PRT) described in greater detail in a commonly assigned co-pending U.S. patent application entitled “APPARATUS AND METHOD FOR SAFELY MAINTAINING A RESTRAINING HOLD ON A PERSON”.

While restraint holds are useful for relatively short periods of time, often, restraint of the EDP is necessary for an extended period. In such cases, the EDP must be restrained using some sort of a mechanical restraint system. Typically, this involves placing wrist and ankle restraints on the EDP so that the EDP may be restrained for an extended period of time at the place of the restraint hold, or transported to another location while wearing the restraints. Also, for extended restraints, special beds with integrated restraints are used in many facilities. Previously known restraint systems involve mechanical locks—for example, the popular Posey TAT restraint utilizes a mechanical spring-loaded lock that require a special key to open. It takes at least 4–5 staff members to successfully apply such restraints at a speed of no lower than 2–3 minutes per restraint. During the application of the restraints the EDP must be held down and poses a constant threat to the staff members until the restraining process is complete. Furthermore, removal of such restraints in emergency situations (i.e. in a medical emergency) takes a significant amount of time since a key must be located and used to open each restraint on each limb—this is especially problematic because without the key, which may not be immediately available in case of an emergency, the restraints cannot be removed at all. Manipulation of the restraints once attached is difficult as well requiring several people to pull webbing through complex system of buckles and connectors. Another problem that often arises, is that a bed with integrated mechanical restrains for restraining the EDP for extended periods of time may not be available when necessary, thus forcing the staff members to find alternate long-term restraint means. Also, complex previously known restraint systems are expensive, heavy, and require extensive training to use properly. This is especially true of beds with integrated restrain systems. Most importantly, sometimes restrained EDPs must be transported by being carried (i.e. when the EDP is sedated, unconscious, or particularly agitated) and this poses difficulty and danger both to the staff members transporting the EDP, and to the EDP themselves.

Finally, in certain cases, when the EDP is restrained for an extended period of time (for example at a bed), the EDP may need to be transported from the bed to another area. This may be required during very urgent circumstances (such as during a fire or other emergency). In this case, the EDP will need to be quickly removed from the bed, and this poses two significant problems. First, the EDP must be released from the bed restraints and new mechanical restraints must be applied. This exposes the staff members to danger from the EDP, because at some point the EDP will be only partially restrained, and also this process can take a very long period of time. Second, the EDP may be sedated or unconscious and unable to move on their own. In case of an emergency, the EDP will need to be carried and, as pointed out above, this poses difficulties and risks. The commonly assigned co-pending patent application entitled “Multi-Point Soft Restraint Apparatus and Method” provides an advantageous solution to the first problem, but does not facilitate solution of the second problem.

Thus, it would be desirable to provide a lightweight and easy to use system for transporting and securing persons that are restrained with mechanical restraints. It would also be desirable to provide a transport and securing system that may be easily deployed onto, and removed from, beds and other stationary structures for long term EDP restraint. It would further be desirable to provide a transport and securing system that is easy to store and transport when not in use. It would also be desirable to provide a transport and securing system that once secured to a stationary structure may be instantaneously disconnected therefrom while maintaining the EDP in full restraints.

SUMMARY OF THE INVENTION

The apparatus of the present invention, and method of use thereof, remedies the problems associated with securing EDPs to stationary structures for long term restraint and with quick removal of the restrained EDP from the stationary structure in case of an emergency. In brief summary, the inventive transport and securing system advantageously provides: (1) quick and easy application to the restrained EDP as well as quick and easy removal in case of an emergency; (2) severe restriction to the range of motion of the EDPs chest, arms and legs; (3) a secure fit to any EDP size; (4) easy and quick releasable attachment to stationary structures; (5) lightweight and simple construction, making the inventive system easy to transport and use; and (6) easy and instant release of the system from connection to a stationary structure in case of an emergency.

The transport and securing system of the present invention is utilized in conjunction with a wrist and ankle mechanical restraint system, which releasably secures the EDP to the transport and securing system, to easily and quickly transport a restrained EDP and secure the EDP to an ordinary bed, or any other stationary structure, without removing the EDP’s mechanical restraints. A instant release mechanism enables a single staff member to immediately disconnect the transport and securing system from the stationary structure so that the EDP may me quickly transported into another location without releasing the EDP from the mechanical restraint system. The inventive transport and securing system includes optional releasable chest and stomach straps to supplement the mechanical restraint system. Alternately, the inventive transport and securing system may be configured to utilize an upper body protection and face shield system disclosed in the commonly assigned co-pending U.S. provisional patent application entitled "Articulated Upper Body Protector Restraint Apparatus and Method" which is hereby incorporated by reference herein in its entirety. When not in use, the inventive transport and securing system rolls up into a compact cylinder for convenient storage and transportation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures.

DESCRIPTION OF THE PREFERRED EMBODIMENTS

The present invention relates to a restrained person transport and securing system that, in conjunction with a mechanical restraint system, may be utilized to easily and quickly transport a restrained subject and secure the subject to an ordinary bed, or any other stationary structure, without removing the subject's mechanical restraints. Furthermore, when not in use, the inventive system rolls up for convenient storage and transportation.

Preferably, the apparatus and method of the present invention are utilized in conjunction with soft circular restraints, such as those disclosed in the commonly assigned co-pending U.S. patent applications entitled, respectively, "Soft Circular Restraint Apparatus and Method" and "Rapid Deployment Soft Restraint Apparatus and Method" which are hereby both incorporated by reference in their entirety. However, the inventive transport and securing system may be utilized with other mechanical restraint systems, if the other systems are provided with appropriate releasable connectors that are configured to releasably connect to the various restraint connectors of the inventive system.

It should be understood that while the present invention refers to Emotionally Disturbed Persons (hereinafter "EDPs") and Staff Members, the inventive techniques and apparatus may be applied in virtually any situation where a subject is being restrained and application of mechanical restraints is warranted. Thus, the present invention is applicable in law enforcement, hospitals, mental health care facilities, drug and alcohol rehabilitation centers, etc.

Furthermore, while description of the present invention refers to connecting to a bed, it should be understood that the point connector elements of the inventive transport and securing system may be advantageously used to connect to any stationary structure where it is desirable to maintain the EDP in a restrained position for an extended period of time.

Figure 5A:
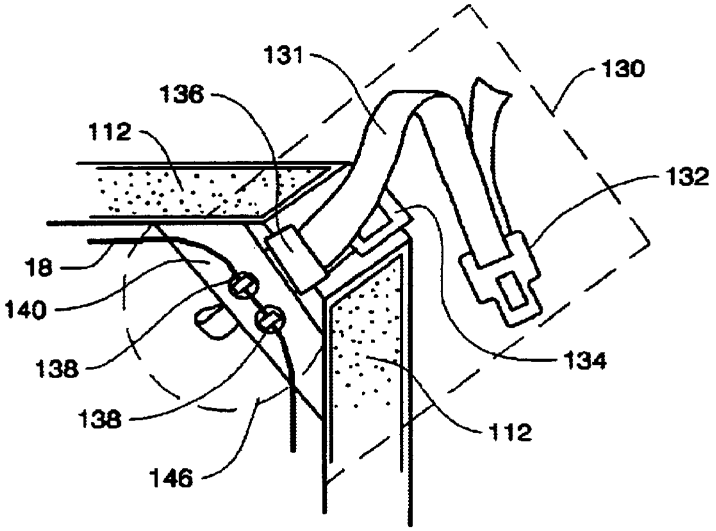
FIG. 5A shows a top view of an exemplary embodiment of a releasable point connector of the inventive transport and securing system of FIG. 1.
Figure 5B:
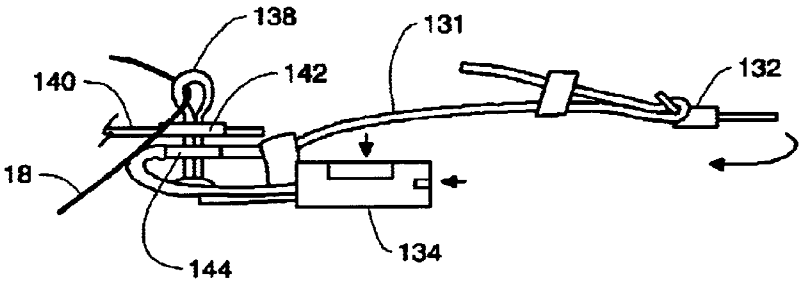
FIG. 5B shows a side view of the releasable point connector of FIG. 5B.

Finally, while a number of exemplary releasable connectors are illustrated in the various drawings, it should be understood that other types of releasable connectors may be used as a matter of design choice without departing from the spirit of the invention. For example, two-part seatbelt-type point connectors used to secure the inventive system to a stationary structure (such as shown in FIGS. 5A and 5B) may be readily replaced by a single carabiner-type connector that along with an attached webbing member can loop around a portion of the stationary structure and releasably connect back to the webbing member thus forming a noose around the stationary structure portion, that may be tightened with an application of a tensioning element to the webbing member.

Before application of any sort of mechanical restraints, it is important that control over the EDP is established by placing the EDP into a restraining hold. The Primary Restraint Technique (hereinafter "PRT") is an advantageous modular single person restraint that is applied by an EDP care professional (hereinafter "staff member") to an EDP from behind. The maneuvers involved in implementing the PRT are described in greater detail in connection with the Primary Restraint Technique (PRT) described in greater detail in a commonly assigned co-pending U.S. patent application entitled "APPARATUS AND METHOD FOR SAFELY MAINTAINING A RESTRAINING HOLD ON A PERSON" which is hereby incorporated by reference in its entirety. It should be noted, however, that the restraint system of the present invention does not require use of the PRT—it may be advantageously be utilized in any situation where the EDP is physically restrained by one or more staff members or other individuals.

Figure 7:
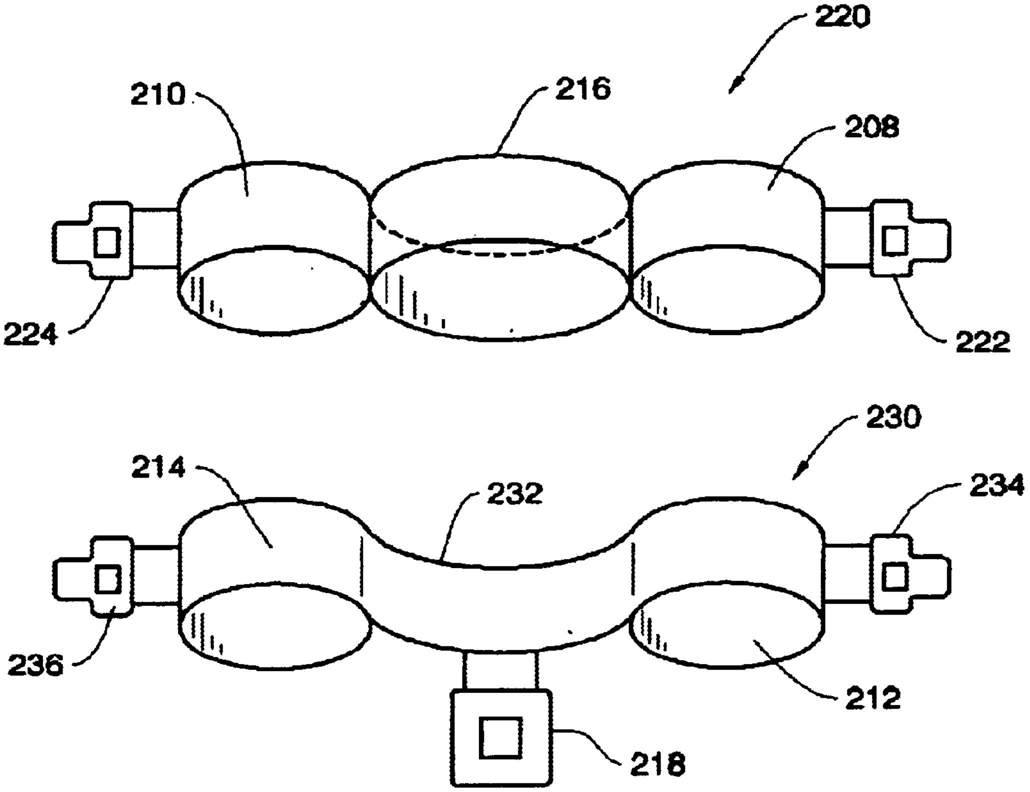
FIG. 7 shows a top-perspective simplified view of mechanical wrist and ankle cuff restraints and interconnects that are applied to a restrained subject and that are used in conjunction with the inventive transport and securing system of FIG. 1.

Referring first to FIG. 7, the transport and securing system of the present invention is used in conjunction with wrist cuff restraint system 220 and an ankle cuff restraint system 230. The wrist cuff restraint system 220 is shown in a simplified form includes two wrist cuff restraints 208, 210, each having a respective releasable connector 222, 224, and an optional waist interconnect 216 connecting the wrist cuff restraints 208, 210 and looping around the EDP's waist thus keeping the wrist cuff restraints 208, 210 close to the EDP's sides. The ankle cuff restraint system 230 is also shown in a simplified form and includes two ankle cuff restraints 212, 214, each having a respective releasable connector 234, 236, and an optional ankle interconnect 232 connecting the ankle cuff restraints 212, 214 optionally supplied with a perpendicularly mounted releasable connector 218.

The wrist and ankle cuff restraint systems 220, 230 are preferably ones disclosed in the above-incorporated commonly assigned U.S. patent applications "Soft Circular Restraint Apparatus and Method" and "Rapid Deployment Soft Restraint Apparatus and Method". However, as a matter of design choice, any mechanical restraint system supplied with releasable connectors 222, 224, 234 and 236 (and optionally connector 218) or the like, may be readily utilized in conjunction with the inventive multi-point restraint connection system, without departing from the sprit of the invention.

Referring now to FIGS. 1–4, a first embodiment of an inventive transport and securing system 10 is shown. The transport and securing system 10 comprises a flexible transport platform 12 configured to receive an EDP 120 on its top surface. The transport platform 12 may be made of any resilient, strong, and easily to clean material, such as nylon or other synthetic. The transport platform 12 comprises at least an upper layer 100 and a separate lower layer 102 of similar size and construction to the upper layer 100, with an optional flexible removable padding layer 104 positioned therebetween. The padding layer 104 may be composed of foam or similar resilient material.

The system 10 also includes a reinforcing webbing system 110 on its lower layer 102 to support the EDP's weight. The reinforcing webbing system 110 is preferably a network of criss-crossing high tensile strength synthetic webbing members (such as nylon webbing) sewn to one another and to the lower layer 102. Four handles 36 are provided (two on each side of the lower layer 102) for enabling two or more staff members to easily carry the EDP disposed thereon. Optionally, the handles 36 may be integrated into (e.g. serve as extensions of) the reinforcing webbing system 110.

Upper layer 100 and lower layer 102 also includes a plurality of releasable connectors 114, 112, respectively which may be any combination of hook/loop material sets, buttons, zippers, etc., disposed around the edges of the upper layer 100 and the bottom layer 102 for releasably securing the layers to one another with the optional padding layer 104 sandwiched therebetween. The exact selection of releasable connector types and their positioning along the edges of the layers 100, 102 is a matter of design choice and may be varies greatly without departing from the spirit of the invention.

Optionally, wrist and leg restraint systems 220, 230 may be stored with the system 10 and releasably connected to the upper layer 100 such that when the system 10 is unrolled, the restraint systems 220, 230 are readily available for use. For this purpose, the system 10 may include optional hook or loop material strips 106 for releasably attaching the wrist restraint system 220 thereto, and hook or loop material strips 108 for releasably attaching the ankle restraint system 230 when the system 10 is in storage. The hook or loop material strips 106, 108 are preferably positioned on the upper layer 100.

The transport and securing system 10 has three primary sets of functional elements. The first set of functional elements is responsible for securing the EDP 120 to the transport platform 12, and includes releasable chest straps 20, supplied with releasable connectors 52, and releasable belly. straps 22 supplied with releasable connectors 50, which are used to secure the upper body of the EDP to the transport platform 12. The releasable connectors 50, 52, which may be snap-in plastic connectors or seatbelt-type connectors are preferably supplied with tensioning mechanisms (not shown) to adjust the size of the straps 20, 22 to the size of the EDP 120.

The first set of functional elements also includes wrist releasable connectors 26, 28 for connecting to corresponding wrist cuff restraints 208, 210 of the wrist restraint system 220, via the restraint connectors 222, 224, ankle releasable connectors 46, 48 for connecting to ankle cuff restraints 212, 214 of the ankle restraint system 230, via the restraint connectors 234, 236, and a leg releasable tensioning connector 34, with an incorporated tensioning device (not shown), for connecting to a releasable connector 218 of the ankle restraint system 230.

Thus, through the use of the first set of functional elements 20, 22, 26, 28, 34, 46, and 48, the EDP 120 may be advantageously releasably secured to the transport platform 12, and subsequently removed therefrom, without ever releasing the EDP 120 from their restraint systems 220, 230.

The second set of functional elements is responsible for securing the system 10 to a bed 122 or to another stationary structure with rigid structural elements, and includes top releasable point connectors 14, 16 with incorporated tensioners (not shown) for securing the top portion of the system 10 to a top portion of the bed 122 (e.g. to the top corners of the bed 122), a central releasable loop 66, supplied with a releasable connector/tensioner set 24, for encircling the bed 122 to secure the middle portion of the system 10 to the bed 122, and bottom releasable point connectors 30, 32 for securing the bottom portion of the system 10 to a bottom portion of the bed 122 (e.g. to the top corners of the bed 122).

Preferably, the point connectors 14, 16, 30, 32 are configured such that they can easily and releasably attach to rigid portions of the bed either via direct connectors (such as carabineers) or via releasable connectors looping around the rigid bed portions and back upon themselves to couple with a secondary connector positioned at the transport platform 12. The point connectors 14, 16, 30, 32 also include tensioning devices (not shown) for ensuring that the system 10 is securely fastened to the bed 122. Other releasable connector configurations may be used as a matter of design choice without departing from the spirit of the invention. An exemplary embodiment of the point connectors 14, 16, 30, 32 is shown in FIGS. 5A and 5B and is described in connection therewith.

Optionally, to aid staff members in distinguishing between the first set of functional elements that are used to connect the EDP 120 to the system 10 and the second set of functional elements that are used to connect the system 10 to the bed 122, the different functional element sets may be color coded. For example, the first set of functional elements 20, 22, 26, 28, 34, 46, and 48 may be colored red, while the second set of functional elements 14, 16, 30, 32, and 66 may be colored blue.

Thus, through the use of the second set of functional elements 14, 16, 30, 32, and 66, the system 10 may be advantageously releasably secured to the bed 122 and subsequently removed therefrom, without ever releasing the EDP from their restraint systems 220, 230 or from the transport platform 12.

The third set of functional elements is responsible for an instant release of the system 10 from a secured position (i.e. when the system 10 is secured to the bed 122) and works in conjunction with the second set of functional elements 14, 16, 30, 32, and 66. Of course, the second set of elements (i.e. point connectors 14, 16, 30, 32 and loop 66) can be released very quickly individually to move the system 10 and the EDP 120 away from the bed 122 without requiring a quick release mechanism. However, in some cases (such as during an emergency—a fire, etc.), an instant release of the system 10 from the bed 122 may be necessary. Each of the second set of functional elements includes a releasable retaining device that releasably secures each element 14, 16, 30, 32 and 66 to the lower layer 102 via a release line 18. The point connectors 14, 16, 30 and 32 include respective releasable retaining devices 58, 60, 54, and 64, while the loop 66 includes two releasable devices 56, 62, one on each side of the lower layer 102. The releasable retaining devices may be of any configuration suitable for use with the release line 18. For example, the retaining device 54 may include one or more strong loops (not shown) secured to the lower layer 102 and passed through corresponding rings defined in the point connector 14 with the line 18 passed through the loops. While the line 18 is in the loops, the point connector 14 is secured to the lower layer 102. When the line 18 is removed, the loops freely pass through the rings causing the point connector 14 to disengage from the lower layer 102. An example of such an arrangement is shown in FIGS. 5A, 5B and described in connection therewith.

The release line 18 loops through each releasable device 54, 56, 58, 60, 62, 64 and secures each respective device to the lower layer 102 thus keeping the securing elements 14, 16, 30, 32 and 66 attached to the system 10 in its normal position. The release line 18 may be any elongated flexible thin member, such as coated or uncoated wire. The line 18 has two ends that freely rest in the bottom portion of the lower layer 102 proximal to the releasable retaining devices 54, 64.

A portion of the line 18 is accessible to a staff member outside of the system 10 via a tab 116. In an emergency, a staff member may pull on the tab 116 and immediately remove the release line 18 from the system 10. This will instantly release and disconnect all the releasable retaining devices 54, 56, 58, 60, 62, 64 and thus the second set of functional elements 14, 16, 30, 32, and 66 from the system 10 and enable the system 10 to be instantly transported away from the bed 122 with the EDP 120 still secured thereon. To return the system 10 to its previous state the disconnected functional elements 14, 16, 30, 32, and 66 are placed back into the system 10 and the line 18 is threaded through all the releasable retaining devices 54, 56, 58, 60, 62, and 64.

Figure 1:
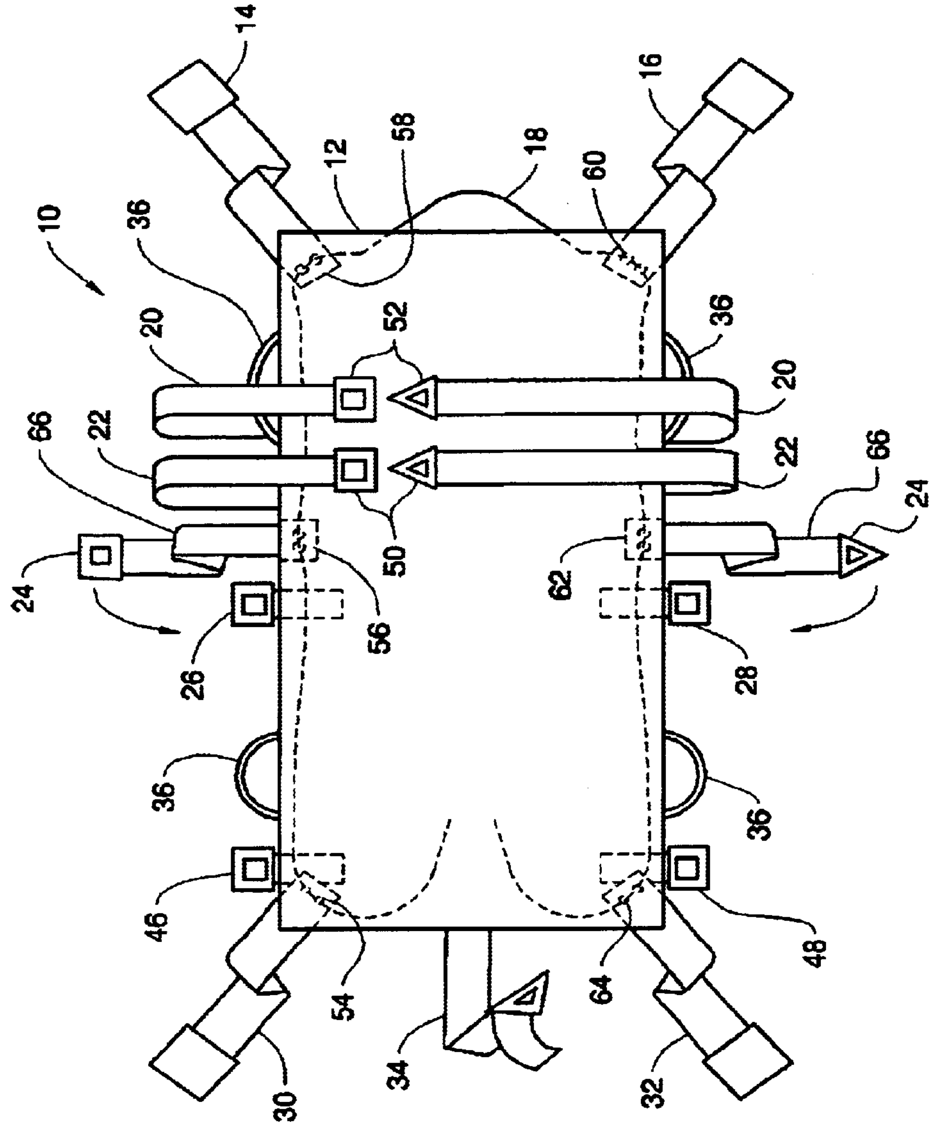
FIG. 1 shows a top view of a first embodiment of a system for transporting and securing restrained subjects of the present invention.
Figure 2:
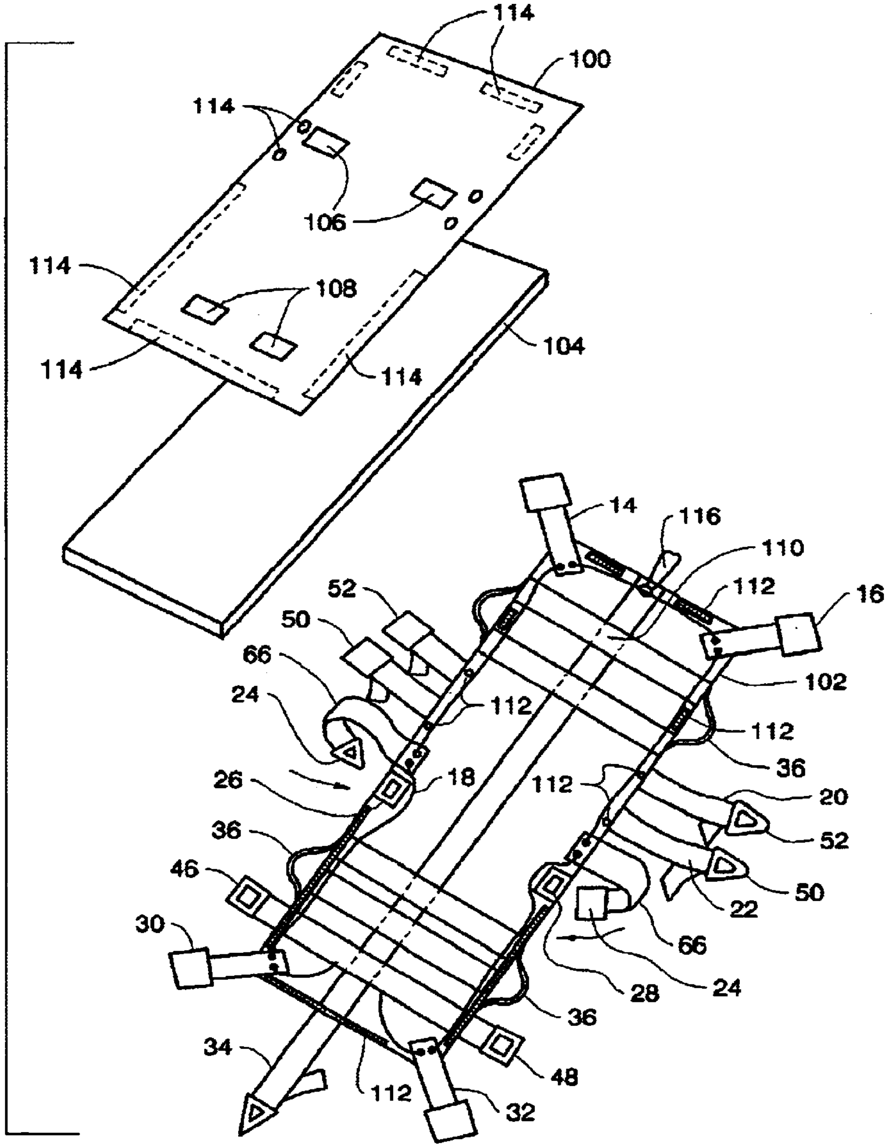
FIG. 2 shows a top-isometric exploded view of a disassembled inventive transport and securing system of FIG. 1.
Figure 3:
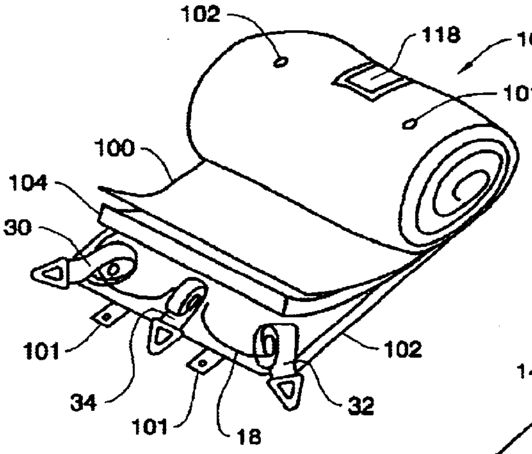
FIG. 3 shows a top-isometric view of the inventive transport and securing system of FIG. 1 in a partially stored position.
Figure 4:
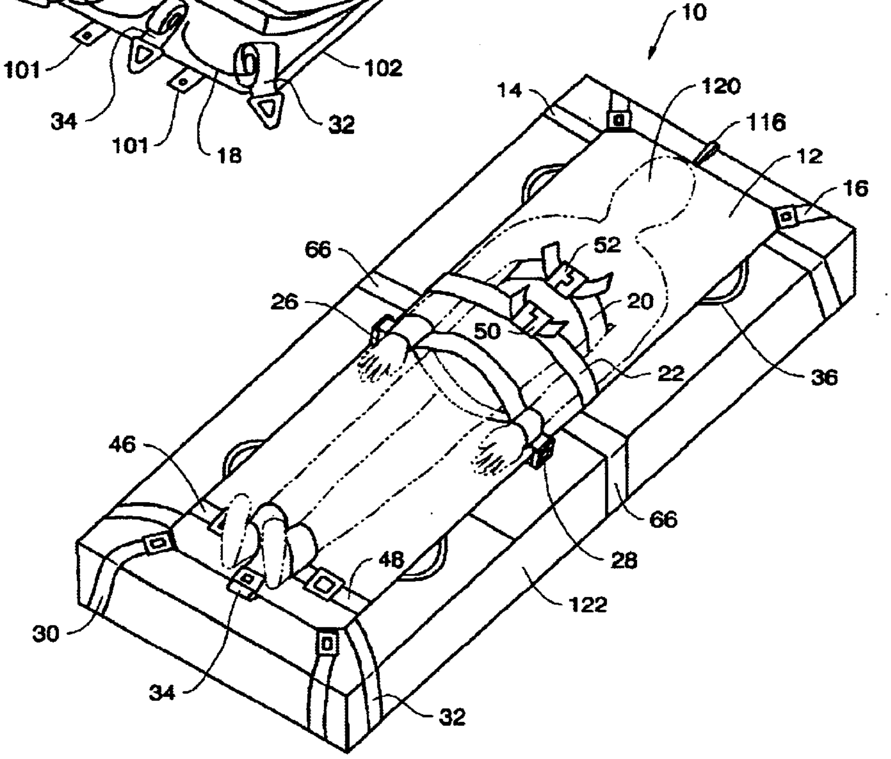
FIG. 4 shows a top-isometric view of the inventive transport and securing system of FIG. 1 deployed on a subject and connected to a stationary structure.

The system 10 and the layers 100, 102 are preferably configured such that the various restraint connectors 26, 28, 34, 46, 48 and point connectors 14, 16, 30, 32 may be withdrawn between the layers 100 and 102 and folded therein for storage when the system 10 is not in use (as shown in FIG. 3). Resilient loops (not shown) disposed on the various connectors may be provided to facilitate folding and storage of the connectors. Furthermore, releasable closure devices (not shown) such as matching hook and loop material strops may be provided adjacent to the connectors to retain the folded connectors between the layers 100, 102.

When not is use, the system 10 may be easily rolled up into a small light cylinder (as sown in FIG. 3) and easily carried and/or stored. Retaining connectors (such as button connectors 101) may be provided for the system 10 to keep it in its rolled-up state for storage. An external pocket 118 may be provided on the outer surface of the layer 102 for a card that may serve to log signatures of users and dates of use for record-keeping. The system 10 is further advantageous because it can be taken apart easily and the various parts (such as layers 100, 102 and the various connectors) may be readily washed using normal washing machines.

Referring now to FIGS. 5A and 5B an exemplary embodiment of a point restraint connector 131 (such as connector 14, 16, 30 or 32) is shown. The connector 131 includes an elongated webbing member 131 terminating in a female seatbelt-type connector/tensioner 132 on one end and secured to the lower layer 102 on the other end. A male seatbelt-type connector 138 is positioned at the corner of the lower layer 102 below the webbing member 131. An elastic loop 136 is provided for stowing the folded member 121 when the system 10 is not is use. During use the webbing member 131 is looped around a structural portion of the bed 122 and releasably connected back to the connector 138. Tension is then adjusted using the connector/tensioner 132 to tightly secure the point connector 130 to the bed 122. A releasable retaining device 146 includes a pair of strong loops 138 secured to the lower layer 102 and passed through corresponding rings 144 defined in the point connector 130 and rings 142 defined in a securing webbing element 140 with the line 18 passed through the loops 138. While the line 18 is in the loops 138, the point connector 130 is secured to the lower layer 102. When the line 18 is removed, the loops 138 freely pass through the rings 142, 144 causing the point connector 130 to disengage from the lower layer 102.

Figure 6A:
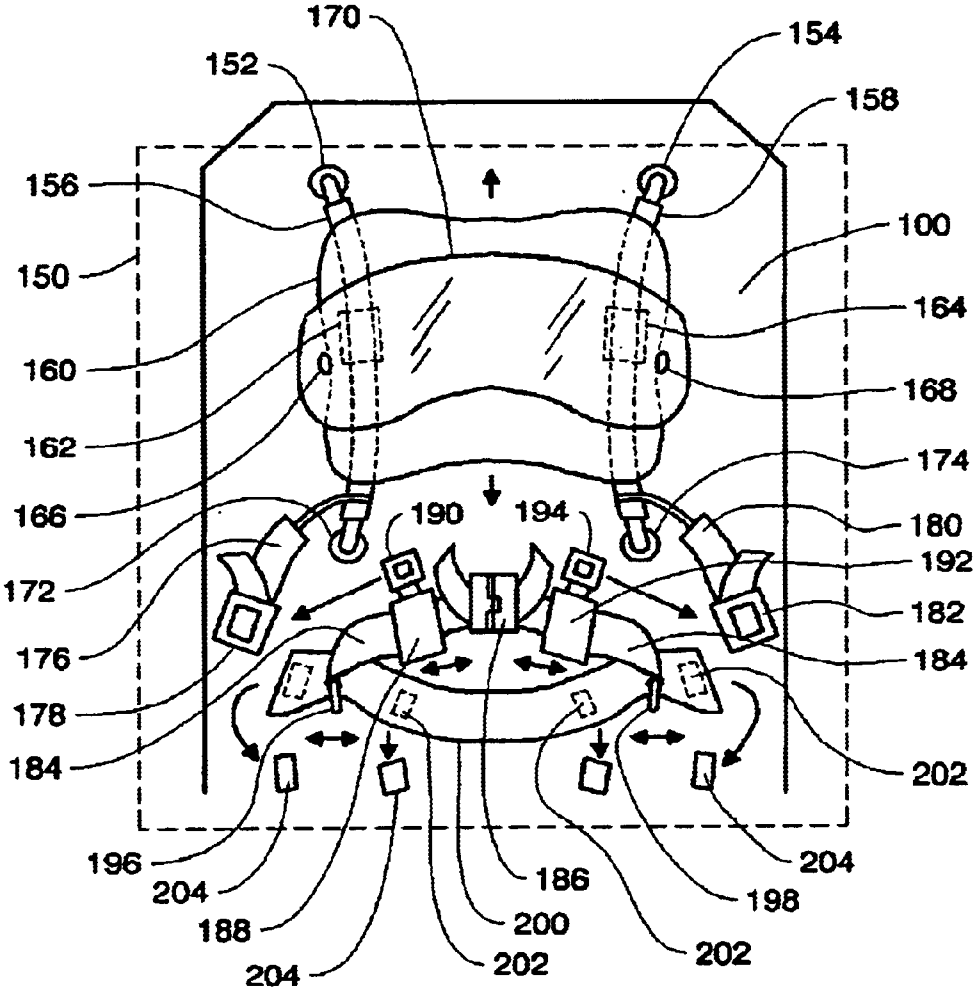
FIG. 6A shows a top view of an exemplary embodiment of an upper body and face protection system used in conjunction with the inventive transport and securing system of FIG. 1.
Figure 6B:
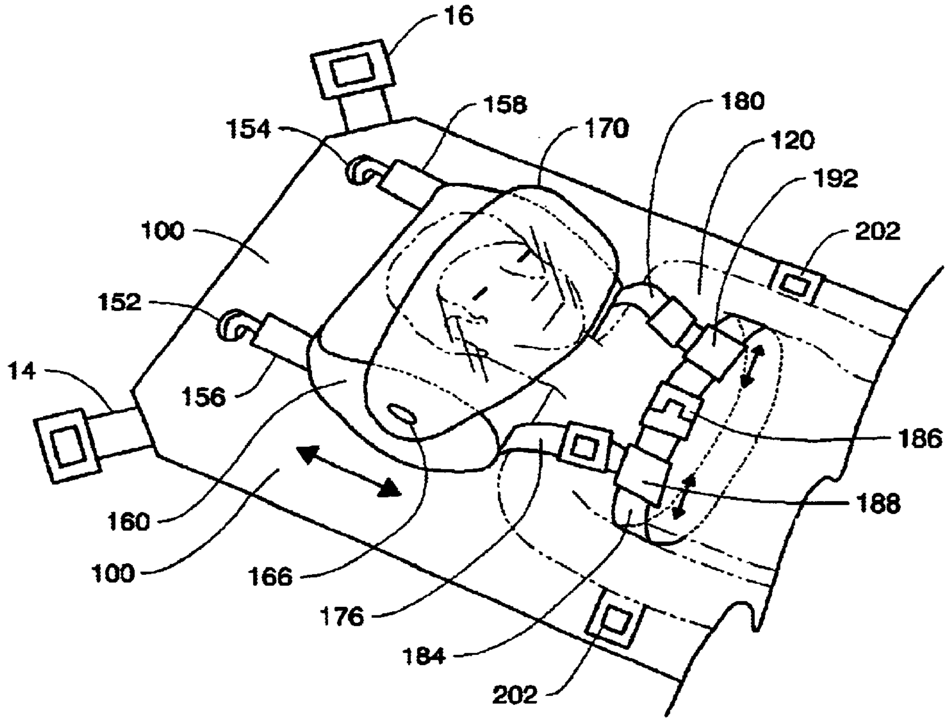
FIG. 6B shows a top isometric view of the upper body and face protection system of FIG. 6A.

Referring, now to FIGS. 6A and 6B, an optional upper body protection system 150 is shown that may be used to replace the chest and stomach loops 20 and 22. The upper body protection system 150 is a modified version of the system shown and described in the above-incorporated U.S. provisional patent application "Articulated Upper Body Protector Restraint Apparatus and Method".

The upper body protection system 150 includes two flexible rail elements 156, 158 secured to the lower layer 102 through holes 152, 172 and 154, 174, respectively defined in the upper layer 100 (the rail elements pass through the padding layer 104 if it is utilized). A contour pillow 160 is slidably mounted on the rails 156, 158 via a pair of sheaths 162, 164. Optionally, the contour pillow 160 may be replaced by an elastic harness with an ordinary pillow held therein (not shown). A pair of shoulder elements 176, 180 are slidably mounted on the bottom portions of the respective rails 156, 158 below the pillow 160. Each shoulder element is supplied with a respective releasable connector/tensioner 178, 182. A support webbing element 200, positioned under the back of the EDP 120, is releasably connected to the lower layer 102 via releasable connectors 202 (such as one-directional snap-buttons) through holes 204 defined in the upper layer 100 (and through the padding layer 104). When the support element 200 is connected to the lower layer 102, two sliding zones are defined by the support element 200 at the sides of the upper layer 100.

A chest belt 184 having a rigid loop 196 at one end and a rigid loop 198 at the other end is looped over the EDP's chest with each rigid loop 196, 198 sliding freely in its own corresponding sliding zone defined by the support webbing element 200. The chest belt 184 includes a centrally positioned releasable connector 186 with integrated tensioners. A sliding shoulder loop 188 is slidably mounted on the chest belt 184 between the rigid loop 196 and the chest connector 186. The shoulder loop 188 includes a releasable connector 190 for connecting to the respective connector/tensioner 178 to secure the EDP's shoulders to the upper layer 100. A sliding shoulder loop 192 is slidably mounted on the chest belt 184 between the rigid loop 198 and the chest connector 186. The shoulder loop 192 includes a releasable connector 194 for connecting to the respective connector/tensioner 182 to secure the EDP's shoulders to the upper layer 100.

The comfort pillow 160 may optionally include releasable connectors 166, 168 to releasably secure a clear bite/spit guard 170 to the comfort pillow 160 thus preventing the EDP 120 from spitting at or biting staff members while enabling EDP to see their surroundings. The upper body protection system 150 advantageously and comfortably secures the EDP to the system 10 regardless of the EDP 120 size or movement.

Because all elements of the inventive system 10 are flexible and soft, the EDP will not hurt themselves or experience significant discomfort by struggling against the restraints. Most importantly, the inventive system 10 can be easily released in one second in an emergency situation without need for a special key. Moreover, the securing and transport system 10 of the present invention is easy and intuitive to use and relatively inexpensive to manufacture. Finally, the construction of the inventive securing and transport system 10 makes it easy to deploy in any setting and with any stationary structure, such as a bed, even one that is not designed for use with restraints.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

I claim:

1. A transport and securing apparatus for transporting a person restrained with a mechanical restraint system and for securing the restrained person to a stationary structure, the mechanical restraint system comprising a plurality of limb cuff restraints each having a releasable cuff connector, the apparatus comprising:

a flexible transport platform sized and configured to receive and hold the restrained person thereon;

first releasable connector means for releasably connecting the plural limb cuff restraints to said transport platform thereby releasably securing the restrained person on said transport platform; and second releasable connector means for releasably connecting said transport platform to the stationary structure to thereby secure the restrained person to the stationary structure.

2. The apparatus of claim 1, further comprising quick release means, connected to said second releasable connector means, for instantly disengaging said second releasable connector means from the stationary structure thereby enabling rapid removal of said transport platform from the stationary structure.

3. The apparatus of claim 1, further comprising at least one supplemental restraint device operable to secure at least one of the person's chest and stomach to said transport platform.

4. The apparatus of claim 1, further comprising at least two pairs of handles, each pair positioned at one of the longitudinal sides of said transport platform.

5. The apparatus of claim 1, wherein said transport platform comprises an upper layer, having an top and bottom surface and circumferential edges, for receiving the restrained person on said top surface thereof, and a lower layer, having an top and bottom surface and circumferential edges, wherein said first and second releasable connector means are securely positioned on said top surface of said lower layer, proximal to said edges of said lower layer.

6. The apparatus of claim 5, further comprising reinforcing means positioned on one of said top and said bottom surfaces of said second layer for improving tensile strength of said lower layer.

7. The apparatus of claim 5, further comprising third releasable connection means, positioned proximal to said circumferential edges on said bottom surface of said upper layer and said top surface of said lower layer.

8. The apparatus of claim 7, wherein said third releasable connection means comprises at least one set of releasable connectors selected from the group of: hook and loop material strips, zippers, sliding clasps, and button clasps.

9. The apparatus of claim 7, further comprising a removable flexible padding layer, smaller than said upper and lower layers and disposed between said upper and lower layers, that improves the comfort of the restrained person placed on said upper layer, wherein said padding layer is secured between said upper and lower layers by said third releasable connection means.

10. The apparatus of claim 9, wherein said padding layer is composed of synthetic foam.

11. The apparatus of claim 5, wherein said first releasable connector means comprises:

(1) a first pair of releasable connectors, substantially centrally positioned at each longitudinal side of said second layer, operable to releasably connect to the releasable limb cuff connectors corresponding to the restrained person's wrists, when the restrained person is placed on said upper layer, and (2) a second pair of releasable connectors, each comprising a first elongated webbing member, positioned at each longitudinal side of said second layer proximal to an expected location of the restrained person's ankles, operable to releasably connect to the releasable limb cuff connectors corresponding to the restrained person's ankles, when the restrained person is placed on said upper layer.

12. The apparatus of claim 11, wherein the limb cuff connectors comprise an interconnect therebetween having a releasable connector thereon, said first releasable connector means further comprises:

(3) a releasable tensioning connector, substantially centrally positioned at a bottom side of said second layer, operable to releasably connect to the releasable interconnect connector, when the restrained person is placed on said upper layer.

13. The apparatus of claim 5, wherein said second releasable connector means comprises:

(1) a third pair of releasable connectors each comprising a second elongated webbing member, positioned at two top corners of said top surface of said lower layer, operable to releasably connect to a head portion of the structure, when the restrained person is placed on said upper layer and said transport platform is placed on the structure, and (2) a fourth pair of releasable connectors, each comprising a third elongated webbing member, positioned at two bottom corners of said top surface of said lower layer, operable to releasably connect to a foot portion of the structure, when the restrained person is placed on said upper layer and said transport platform is placed on the structure.

14. The apparatus of claim 13, wherein said second releasable connector means further comprises:

(3) a belt connector having two ends and comprising a releasable clasp and at least one tensioning element, having each end substantially centrally positioned on one of said longitudinal sides of said second layer, said belt connector being operable to connect a central region of said transport platform to the structure when the restrained person is placed on said upper layer and said transport platform is placed on the structure, by passing said belt connector below the structure and engaging said releasable clasp.

15. The apparatus of claim 14, wherein each of said third pair and said fourth pair of releasable connectors, and said belt connector, comprises elastic means for retaining said third pair and said fourth pair of releasable connectors and said belt connector between said upper and said lower layers when not in use, wherein said third releasable connection means comprises a plurality of open regions corresponding to positions of said third pair and said fourth pair of releasable connectors, and said belt connector, such that said third pair and said fourth pair of releasable connectors, and said belt connector may be withdrawn from between said upper and lower layers during use.

16. The apparatus of claim 14, further comprising an instant release means for instantly disengaging said third pair and said fourth pair of releasable connectors, and said belt connector from said transport platform, comprising a plurality of ring assemblies each connected to each one of said third pair and said fourth pair of releasable connectors, and said belt connector, and a plurality of loops connected to said lower layer upper surface, wherein said plural loops are passed through said rings, and wherein an elongated flexible release line is passed through said loops thus securing said third pair and said fourth pair of releasable connectors, and said belt connector to said lower layer, wherein to activate said instant release means, said release line is pulled from said plural loops thus instantly disengaging said third pair and said fourth pair of releasable connectors, and said belt connector from said lower layer.

17. The apparatus of claim 16, wherein said release line further comprises a tab member to facilitate rapid pulling thereof.

18. The apparatus of claim 1, further comprising an articulated head, chest and shoulder protection device comprising a releasable webbing network attached to an upper surface of said transport platform and aligned with the restrained person's chest, shoulders and head, operable to releasably retain the person's chest and shoulders in a comfortable position, and a support pillow adjustably mounted on said webbing network operable to support the person's head and neck.

19. The apparatus of claim 18, further comprising a clear flexible face shield releasably attached to said support pillow operable to provide protection form spitting and biting by the restrained person.

20. A method for transporting a person restrained with a mechanical restraint system and for securing the restrained person to a stationary structure, the mechanical restraint system comprising a plurality of limb cuff restraints each having a releasable cuff connector, the method comprising the steps of:

(a) providing a flexible transport platform sized and configured to receive and hold the restrained person thereon;

(b) positioning the restrained person on said transport platform;

(c) releasably connecting the plural limb cuff restraints to said transport platform through a first set of releasable connectors, thereby releasably securing the restrained person on said transport platform; and (d) releasably connecting said transport platform to the stationary structure through a second set of releasable connectors to thereby secure the restrained person to the stationary structure.

21. The method of claim 20, further comprising the step of (e) providing a quick release device connected to said second set of connectors; and (f) when necessary, activating said quick release device to instantly disengage said second set of connectors from the stationary structure thereby enabling rapid removal of said transport platform from the stationary structure.

22. The method of claim 21, further comprising the step of (g) providing a releasable closure device on a bottom surface of said transport platform, and (h) when not in use, rolling said transport platform along its longitudinal axis into a substantially cylindrical shape; and (i) engaging said releasable closure device to secure the transport platform in said cylindrical shape.

* * * * *